United States Patent [19]

Yamada et al.

[11] 4,127,673

[45] Nov. 28, 1978

[54] COMBATING FUNGI WITH NEW N-4-HALOBENZYL-N-CYCLOALKYL-N'-PHENYLUREAS AND THIOUREAS

[75] Inventors: Yasuo Yamada; Junichi Saito; Tatsuo Tamura; Yoshio Kurahashi, all of Tokyo, Japan

[73] Assignee: Nihon Tokushu Noyaku Seizo K.K., Tokyo, Japan

[21] Appl. No.: 816,979

[22] Filed: Jul. 19, 1977

[30] Foreign Application Priority Data

Jul. 20, 1976 [JP] Japan .................................. 51/85582

[51] Int. Cl.² ...................... A01N 9/12; C07C 127/15; C07C 157/05
[52] U.S. Cl. ................................ 424/322; 260/552 R; 260/553 A
[58] Field of Search .................. 424/322; 260/553 A, 260/552 R

[56] References Cited

U.S. PATENT DOCUMENTS

| | | |
|---|---|---|
| 3,483,296 | 12/1969 | Martin et al. ..................... 260/553 A |
| 3,660,484 | 5/1972 | Martin et al. ..................... 260/553 A |
| 4,007,033 | 2/1977 | Singer .............................. 260/553 A |
| 4,010,281 | 3/1977 | Yamada et al. .................. 260/553 A |

*Primary Examiner*—V. D. Turner
*Attorney, Agent, or Firm*—Sprung, Felfe, Horn, Lynch & Kramer

[57] ABSTRACT

N-4-halobenzyl-N-cycloalkyl-N'-phenylureas and thioureas of the formula

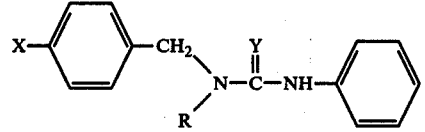

(I)

in which
R is cycloalkyl or methyl-cycloalkyl,
X is halogen, and
Y is oxygen or sulfur,
which possess fungicidal properties.

10 Claims, No Drawings

COMBATING FUNGI WITH NEW N-4-HALOBENZYL-N-CYCLOALKYL-N'-PHENYLUREAS AND THIOUREAS

The present invention relates to and has for its objects the provision of particular new N-4-halobenzyl-N-cycloalkyl-N'-phenylureas and thioureas which possess fungicidal properties, active compositions in the form of mixtures of such compounds with solid and liquid dispersible carrier vehicles, and methods for producing such compounds and for using such compounds in a new way especially for combating pests, e.g. fungi, with other and further objects becoming apparent from a study of the within specification and accompanying examples.

It is known from Japanese Patent Publication No. 29252/1969 that urea compounds of the general formula

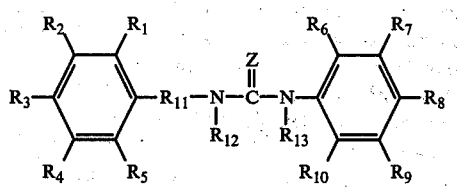

have insecticidal, acaricidal, fungicidal and/or herbicidal activities. In this general formula, Z represents an oxygen or sulfur atom, $R_1$, $R_2$, $R_3$, $R_4$, $R_5$, $R_6$, $R_7$, $R_8$, $R_9$ and $R_{10}$, which may be the same or different, each represents a hydrogen atom, a lower alkyl radical, a lower alkoxy radical or a nitro radical, with the proviso that at least two of the $R_1$–$R_5$ radicals and at least two of the $R_6$–$R_{10}$ radicals are not hydrogen atoms, $R_{11}$ represents a straight chain alkylene radical, and $R_{12}$ and $R_{13}$ each independently represents a hydrogen atom or a lower alkyl radical.

The present invention provides novel urea or thiourea compounds of the general formula

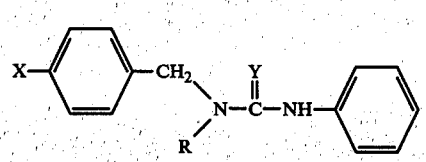

in which
R is cycloalkyl or methyl-cycloalkyl,
X is halogen, and
Y is oxygen or sulfur.

Generally, R is methyl-substituted or unsubstituted cycloalkyl of 3 to 7 carbon atoms, e.g. cyclopropyl, cyclobutyl, cyclopentyl, cyclohexyl or cycloheptyl. X is fluorine or iodine, or preferably chlorine or bromine.

As is shown in the general formula (1), the novel N-4-halogenobenzyl-N-cycloalkyl(or methyl substituted cycloalkyl) N'-phenylurea(or thiourea) compounds of the invention are structually characterized in that one nitrogen is attached to a benzyl which is substituted by halogen in the para-position, and is also attached to a cycloalkyl which may be substituted by methyl, while the other nitrogen is attached to an unsubstituted phenyl.

As compared with known active compounds having somewhat similar structure or activities, the novel compounds according to the invention are characterized by greatly improved technical effects and by very low toxicities to warm-blooded animals. The present compounds are accordingly very useful.

The compounds according to the invention, which have high activities for combating various kinds of phytopathogenic fungi and for inhibiting their multiplication, can be used to protect plants from damage caused by fungi. Particularly, these compounds are highly effective for the control of phytopathogenic Basidiomycetes, for instance those causing sheath blight and seedling-rot diseases of rice plants.

The active compounds according to the present invention can be used against parasitic fungi which infect above-ground parts of plants, pathogenic fungi which attack plants through soil to cause tracheomycosis, seed-borne causative pathogenic fungi and also against soil-borne causative fungi. p These active compounds can be advantageously employed as agricultural and horticultural chemicals against the pathogenic diseases of plants, since they show only a low toxicity to warm-blood animals and have excellent compatibility with higher plants; they do not deleteriously affect cultivated plants at the concentrations usually employed.

Thus, the active compounds can be effectively used for controlling various phytopathogenic fungi such as Archimycetes, Phycomycetes, Ascomycetes, Basidiomycetes, *Fungi Imperfecti* and the like. Particularly, the active compounds show remarkable activities against fungi causing sheath blight (*Pellicularia sasakii*) and seedling rot (*Pellicularia filamentosa*), which are serious diseases of rice plants. In addition, the active compounds are effective for the control of the following diseases of crop plants: sclerotial blight (*Corticium centrifugum*), blast (*Pyricularia oryzae*), rice bacterial leaf blight (*Xanthomonas oryzae*), Chinese cabbage slimy soft rot (*Erwinia aroidaea*), citrus canker (*Xanthomonas citri*), rice helminthosporium leaf spot (*Cochliobolus miyabeanus*), banana leaf spot (*Mycosphaerella musicola*), gray mould of strawberry and the like (*Botrytis cinerea*), grape downy mildew (*Plasmopara viticola*), anthracnosis of grape, apple and pear (*Glomella cingulata*), sclerotinia rot of vegetables (*Sclerotinia sclerotiorum*), anthracnosis of melons (*Colletotrichum lagenarium*), citrus melanosis, (*Diaporthe citri*), apple powdery mildew (*Podosphaera leucotricha*), cucumber powdery mildew (*Sphaerotheca fuliginea*), black spot such as apple leaf spot (*Alternalia mali*), potato early blight (*Alternalia solani*) and pear black spot (*Alternalia Kikuchiana*), and scab, such as apple scab (*Venturia inaequalis*) and pear scab (*Venturia pirina*).

Due to the excellent fungicidal properties mentioned above, the active compounds according to the present invention can also be employed with advantageous results for controlling diseases caused by phytopathogenic fungi which hitherto had to be controlled by such fungicides as those containing heavy metals, arsenic or mercury which are deleterious to human beings and domestic animals.

The present invention also provides a process for the preparation of a compound of the general formula (1), in which:

(a) an amine of the general formula

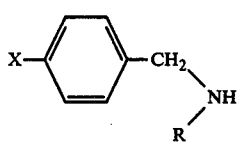

in which R and X have the meanings given above, is reacted with a phenylisocyanate (or isothiocyanate) of the general formula

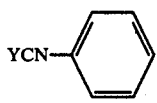

in which Y has the meaning given above or (b) a carbamoyl (or thiocarbamoyl) chloride of the general formula

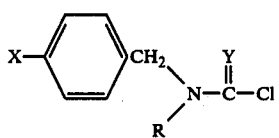

in which X, R and Y are defined as above, is reacted with an aniline.

The process variants (a) and (b) of the invention are further described below.

Process (a)

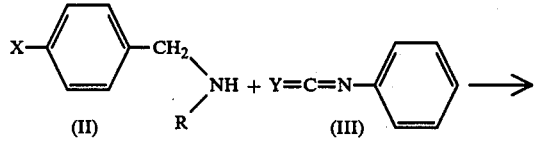

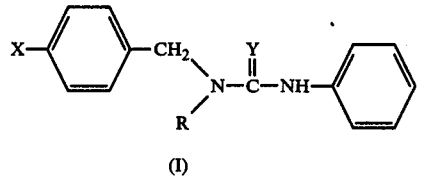

Examples of amines of the general formula (II) include:

N-[4-chloro(or bromo)benzyl]-N-cyclopentylamine,
N-(4-chlorobenzyl)-N-cyclohexylamine,
N-(4-chlorobenzyl)-N-2(or 4-)methylcyclohexylamine, and
N-(4-chlorobenzyl)-N-cycloheptylamine.

The compounds of the general formula (III) are phenylisocyanate and phenylisothiocyanate. The process variant (a) is illustrated by the following reaction scheme:

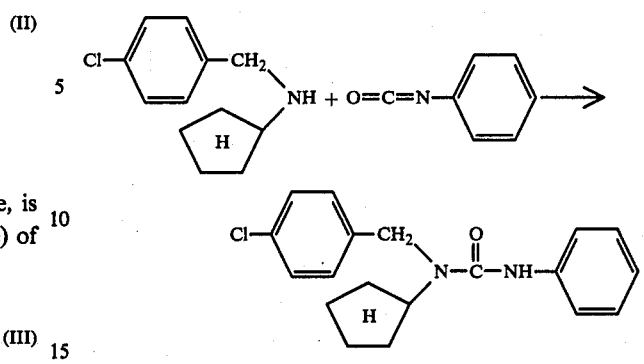

The process is preferably carried out in the presence of a solvent or diluent. For this purpose, any solvent or diluent may be employed.

Examples of these solvents and diluents are water: aliphatic and aromatic hydrocarbons which may optionally be chlorinated, for instance hexane, cyclohexane, petroleum ether, ligroin, benzene, toluene, xylene, methylene chloride, chloroform, carbon tetrachloride, ethylene chloride, trichloroethylene and chlorobenzene: ethers for instance diethyl ether, methyl ethyl ether, di-iso-propyl ether, dibutyl ether, propylene oxide, dioxane and tetrahydrofuran; ketones, for instance acetone, methyl ethyl ketone, methyl iso-propyl ketone and methyl iso-butyl ketone; nitriles, for instance acetonitrile, propionitrile and acrylonitrile; esters, for instance ethyl acetate and amyl acetate; acid amides, for instance dimethylformamide and dimethylacetamide; sulfones and sulfoxides, for instance dimethyl sulfoxide and sulfolane; and bases, for instance pyridine.

The process variant (a) can be carried out over a wide range of temperatures. Generally, the reaction is carried out at a temperature of $-20°$ C. to the boiling point of the reaction mixture, preferably $0°$ C. to $100°$ C. The reaction is preferably carried our under ambient pressure, but it can be operated under elevated or reduced pressures.

Process (b)

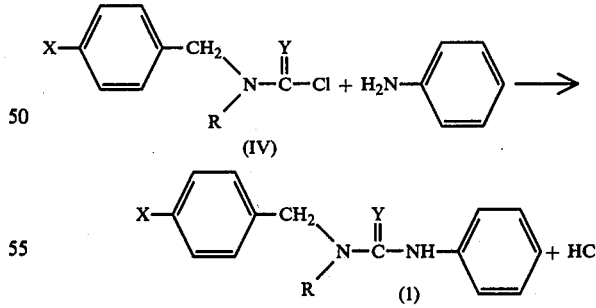

Examples of carbamoyl chlorides or thiocarbamoylchlorides of the general formula (IV) include:

N-[4-chloro(or bromo)benzyl]-N-cyclopentyl-,
N-(4-chlorobenzyl)-N-cyclohexyl-,
N-(4-chlorobenzyl)-N-[2-(or 4-)methylcyclohexyl]-, and
N-(4-chlorobenzyl)-N-cycloheptyl--carbamoylchloride or thiocarbamoylchloride.

The process variant (b) is illustrated by the following reaction scheme:

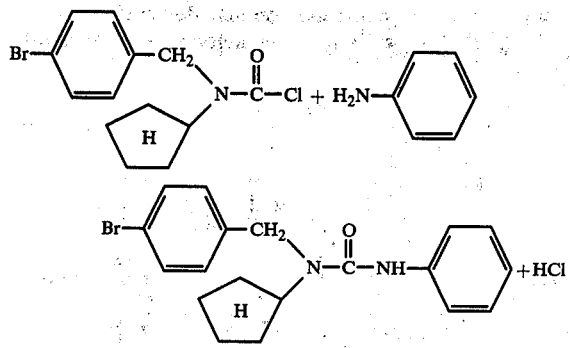

In this process variant, it is possible to use the solvents or diluents as mentioned for process (a).

The process (b) can be carried out in the presence of an acid binding agent. Examples of such acid-binding agents are conventional agents such as alkali hydroxides, carbonates, bicarbonates, alcoholates and tert. organic bases, for example triethyl amine, dimethyl aniline and pyridine.

Like the process (a), the process (b) can be carried out over a wide range of temperatures. Generally, it is carried out at a temperature of −20° C. to the boiling point of the reaction mixtures, preferably 0° C. to 100° C.

The reaction is preferably carried out under ambient pressure but it can also be operated under elevated or reduced pressures.

The active compounds according to the instant invention can be utilized, if desired, in the form of the usual formulations or compositions with conventional inert (i.e. plant compatible or herbicidally inert) pesticide diluents or extenders, i.e. diluents, carriers or extenders of the type usable in conventional pesticide formulations or compositions, e.g. conventional pesticide dispersible carrier vehicles such as gases, solutions, emulsions, suspensions, emulsifiable concentrates, spray powders, pastes, soluble powders, dusting agents, granules, wettable powders, tablets, smoking agents, fumigants, etc. These are prepared in known manner, for instance by extending the active compounds with conventional pesticide dispersible liquid diluent carriers and/or dispersible solid carriers optionally with the use of carrier vehicle assistants, e.g. conventional pesticide surface-active agents, including emulsifying agents and/or dispersing agents, whereby, for example, in the case where water is used as diluent, organic solvents may be added as auxiliary solvents. The following may be chiefly considered for use as conventional carrier vehicles for this purpose: aerosol propellants which are gaseous at normal temperatures and pressures, such as dichlorodifluoromethane or trichlorofluoromethane; inert dispersible liquid diluent carriers, including inert organic solvents, such as aromatic hydrocarbons (e.g. benzene, toluene, xylene, alkyl naphthalenes, etc.), halogenated, especially chlorinated, aromatic hydrocarbons (e.g. chlorobenzenes, etc.), cycloalkanes, (e.g. cyclohexane, etc.), paraffins (e.g. petroleum or mineral oil fractions), chlorinated aliphatic hydrocarbons (e.g. methylene chloride, chloroethylenes, etc.), alcohols (e.g. methanol, ethanol, propanol, butanol, glycol, etc.) as well as ethers and esters thereof (e.g. glycol monomethyl ether, etc.), amines (e.g. ethanolamine, etc.), amides (e.g. dimethyl formamide, etc.), sulfoxides (e.g. dimethyl sulfoxide, etc.), acetonitrile, ketones (e.g. acetone, methyl ethyl ketone, methyl isobutyl ketone, cyclohexanone, etc.), and/or water; as well as inert dispersible finely divided solid carriers, such as ground natural minerals (e.g. kaolins, clays, alumina, silica, chalk, i.e. calcium carbonate, talc, attapulgite, montmorillonite, kieselguhr, etc.) and ground synthetic minerals (e.g. highly dispersed silicic acid, silicates, e.g. alkali silicates, etc.); whereas the following may be chiefly considered for use as conventional carrier vehicle assistants, e.g. surface-active agents, for this purpose: emulsifying agents, such as non-ionic and/or anionic emulsifying agents (e.g. polyethylene oxide esters of fatty acids, polyethylene oxide ethers of fatty alcohols, alkyl sulfates, alkyl sulfonates, aryl sulfonates, albumin hydrolyzates, etc., and especially alkyl arylpolyglycol ethers, magnesium stearate, sodium oleate, etc.); and/or dispersing agents, such as lignin, sulfite waste liquors, methyl cellulose, etc.

Such active compounds may be employed alone or in the form of mixtures with one another and/or with such solid and/or liquid dispersible carrier vehicles and/or with other known compatible active agents, especially plant protection agents, such as other fungicides, or insecticides, acaricides, nematicides, bactericides, rodenticides, herbicides, fertilizers, growth-regulating agents, anti-virus agents, bait lures, etc., such as organic phosphate compounds, carbamate compounds, dithio (or thiol) carbamate compounds, organic chlorine-containing compounds, dinitro compounds, organic sulfur- or metal-containing compounds, antiboitic substances, substituted diphenylether compounds, urea compounds and/or triazine compounds, if desired, or in the form or particular dosage preparations for specific application made therefrom, such as solutions, emulsions, suspensions, powders, pastes, and granules which are thus ready for use.

As concerns commercially marketed preparations, these generally contemplate carrier composition mixtures in which the active compound is present in an amount substantially between about 0.1–95% by weight, and preferably 0.5–90% by weight, of the mixture, whereas carrier composition mixtures suitable for direct application or field application generally contemplate those in which the active compound is present in an amount substantially between about 0.0001–20%, preferably 0.005–10%, by weight of the mixture. Thus, the present invention contemplates overall compositions which comprise mixtures of a conventional dispersible carrier vehicle such as (1) a dispersible inert finely divided carrier solid, and/or (2) a dispersible carrier liquid such as an inert organic solvent and/or water, preferably including a surface-active effective amount of a carrier vehicle assistant, e.g. a surface-active agent, such as an emulsifying agent and/or a dispersing agent, and an amount of the active compound which is effective for the purpose in question and which is generally between about 0.0001–95%, and preferably 0.005–95%, by weight of the mixture.

The active compounds can also be used in accordance with the well known ultra-low-volume process with good success, i.e. by applying such compound if normally a liquid, or by applying a liquid composition containing the same, via very effective atomizing equipment, in finely divided form, e.g. average particle diameter of from 50–100 microns, or even less, i.e. mist form, for example by airplane crop spraying techniques. Only up to at most about a few liters/hectare are needed, and often amounts only up to about 3 to 1000 g/hectare, preferably 30 to 600 g/hectare, are sufficient. In this process it is possible to use highly concentrated liquid compositions with said liquid carrier vehicles containing from about 20 to about 95% by weight of the active compound or even the 100% active substance alone, e.g. about 20-100% by weight of the active compound.

Furthermore, the present invention contemplates methods of selectively killing, combating or controlling pests, e.g. fungi, which comprises applying to at least one of correspondingly (a) such fungi, and (b) the corresponding habitat thereof, i.e. the locus to be protected, e.g. to a growing crop, to an area where a crop is to be grown or to a domestic animal, a correspondingly combative or toxic amount, i.e. a fungicidally effective amount, of the particular active compound of the invention alone or together with a carrier vehicle as noted above. The instant formulations or compositions are applied in the usual manner, for instance by spraying, atomizing, vaporizing, scattering, dusting, watering, squirting, sprinkling, pouring, fumigating, application to seed, and the like.

It will be realized, of course, that the concentration of the particular active compound utilized in admixture with the carrier vehicle will depend upon the intended application. Therefore, in special cases it is possible to go above or below the aforementioned concentration ranges.

The unexpected superiority and outstanding activity of the particular new compounds of the present invention are illustrated, without limitation, by the following examples:

EXAMPLE 1

(Compound No. 1)

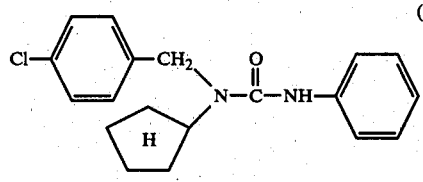

A solution of 12 grams (0.1 mole) of phenylisocyanate in 50 ml of hexane was added dropwise to 21 grams (0.1 mole) of N-4-chlorobenzyl-N-cyclopentylamine in 400 ml of hexane under cooling and stirring conditions. After the addition, the temperature of the reaction mixture was gradually raised, and the solution was then stirred at 50° C. for about 7 hours. The mixture was cooled and filtered. The residue was recrystallized from a mixed solvent of hexane-ethyl alcohol. 31 grams of N-4-chlorobenzyl-N-cyclopentyl-N'-phenylurea were obtained. Yield: 95%. Melting point: 129°-134° C.

EXAMPLE 2

(Compound No. 2)

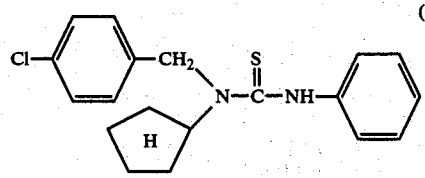

Analogously to Example 1, 21 grams (0.1 mole) of N-4-chlorobenzyl-N-cyclopentylamine were reacted with 13.5 grams (0.1 mole) of phenylisothiocyanate. 32 grams of N-4-chlorobenzyl-N-cyclopentyl-N'-phenylthiourea were obtained. Yield: 92%, Melting point: 129°-132° C.

The urea or thiourea compounds identified in the following table were obtained analogously to Example 1:

Table 1

| Compound No. | R | X | Y | Physical constant (Melting point) |
|---|---|---|---|---|
| 3 | cyclopentyl (H) | Br | S | 129 – 131° C |
| 4 | cyclohexyl (H) | Cl | O | 155.0° C |
| 5 | cyclohexyl (H) | Cl | S | 140 – 143° C |
| 6 | 2-methylcyclohexyl (CH₃, H) | Cl | O | 195 – 196° C |
| 7 | 2-methylcyclohexyl (CH₃, H) | Cl | S | 179 – 180.5° C |
| 8 | 4-methylcyclohexyl (CH₃, H) | Cl | O | 138 – 140° C |
| 9 | 4-methylcyclohexyl (CH₃, H) | Cl | S | 146 – 149° C |
| 10 | cycloheptyl (H) | Cl | O | 143 – 145° C |
| 11 | cycloheptyl (H) | Cl | S | 145 – 147° C |

EXAMPLE 3

(Compound No. 12)

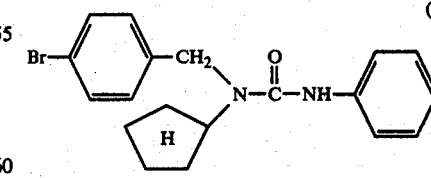

A solution of 32 grams (0.1 mole) of N-4-bromobenzyl-N-cyclopentylcarbamoylchloride in 100 ml of toluene were added dropwise to 19 grams (0.2 mole) of aniline in 400 ml of toluene under cooling and stirring conditions. After the addition, the reaction temperature was gradually raised and the reaction mixture was then stirred at 70°-80° C. for about 10 hours. After cooling, the aniline hydrochloride which had been formed was separated by filtration. The toluene layer was washed with water, with 1% aqueous sodium carbonate, with 1% hydrochloric acid and again with water, and dried with anhydrous sodium sulfate. The toluene was then distilled off. The residue was recrystallized from a mixed solvent of hexane-ethyl-alcohol. 29 grams of N-4-bromobenzyl-N-cyclopentyl-N'-phenylurea were obtained. Yield: 78%. Melting point: 130°–132° C.

EXAMPLE 4

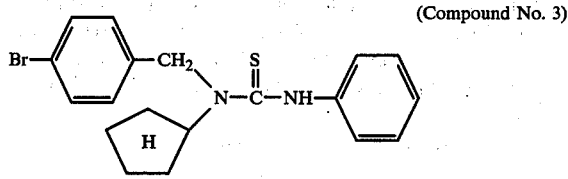

(Compound No. 3)

Analogously to Example 3, 19 grams (0.2 mole) of aniline were reacted with 34 grams (0.1 mole) of N-4-bromobenzyl-N-cyclopentylthiocarbamoyl-chloride, 0.31 grams of N-4-bromobenzyl-N-cyclopentyl-N'-phenylthiourea were obtained. Yield: 80%. Melting point: 129°–131° C.

EXAMPLE 5

(Wettable powder)

50 parts of the compound No. 1 according to the present invention, 45 parts of a 1:5 by weight mixture of diatomaceous earth and kaolinite and 5 parts of emulsifier (polyoxyethylene alkylphenylether) were mixed and ground into wettable powders. They were diluted with water to an active compound concentration of 0.05% and sprayed on to fungi and/or a fungus habitat.

EXAMPLE 6

(Emulsion)

30 parts of compound No. 2 according to the present invention, 30 parts of xylene, 30 parts of high boiling point aromatic hydrocarbons and 10 parts of polyoxyethylenealkylarylether were intimately mixed into an emulsion. This was diluted with water to an active compound concentration of 0.05% by weight and applied by spraying on to fungi and/or a fungus habitat.

EXAMPLE 7

(Dust)

2 parts of compound No. 12 according to the present invention and 98 parts of a 1:3 by weight mixture of talc and clay were mixed to form a dust. This was applied by dusting on to fungi and/or fungus habitat.

EXAMPLE 8

(Dust)

1.5 parts of the compound No. 3 according to the present invention, 0.5 part of isopropyl hydrogen phosphate (PAP) and 98 parts of a 1:3 by weight mixture of talc and clay were mixed to form a dust, and this was applied by dusting on to fungi and/or a fungus habitat.

EXAMPLE 9

(Granules)

To a mixture of 10 parts of the compound No. 4 according to the present invention, 10 parts of bentonite 78 parts of a 1:3 by weight mixture of talc and clay and 2 parts of ligninsulfonate were added 25 parts of water and the whole was intimately mixed. It was finely cut by a pushing-out granulator, made into granular shapes of between 20 and 40 mesh size, dried at a temperature of 40° C.–50° C. and made into granules. They were applied on to fungi and/or fungus habitat by scattering.

EXAMPLE 10

(Granule)

95 parts of clay granules having a granular distribution of between 0.2 and 2 mm were charged into a rotary mixer and evenly wetted by spraying 5 parts of the compound No. 5 according to the present invention (dissolved in an organic solvent) during the rotation. The mixture was then dried at a temperature of 40°–50° C. to form granules. They were scattered on to fungi and/or a fungus habitat.

EXAMPLE 11

(Oily agent)

0.5 part of the compound No. 11 according to the present invention, 20 parts of high boiling point aromatic compounds and 79.5 parts of kerosene were mixed under stirring to form an oily agent and this was scattered on to fungi and/or a fungus habitat.

EXAMPLE 12

Test against *Pellicularia sasakii* (sheath blight):
Pot test Preparation of fungicidal composition
Active compound: 50 parts by weight
Carrier: 45 parts of a 1:5 by weight mixture of diatomaceous earth and kaolin
Emulsifier: 5 parts by weight of polyoxyethylenealkylphenyl-ether The above mentioned amounts of the active compound, the carrier and the emulsifier were mixed with one another to form a wettable powder which was diluted with water to the desired concentration.

Test procedures

Rice plants (Kinmaze variety) were grown in Wagner pots (1/5000 are) under paddy field conditions. When the rice plants formed young ears, the liquid preparation which contained the active compound in the desired concentration was applied thereto in an amount of 100 ml per three pots.

One day after the active compound had been applied the fungus, *Pellicularia sasakii* (which had been grown in a barley medium for 10 days to form its sclerotia), was inoculated upon lower portions of the plants. The plants were kept in a greenhouse at a temperature of 28°–30° C. and at a relative humidity of at least 95%. After that, the degree of infection was evaluated, and the phytotoxicity of the active compound was checked. In this evaluation, the extent of the lesion portion spreading from the inoculation point (which was on the lower portion of the plant) was measured, and then the following calculation was made:

$$\text{Degree of infection (\%)} = \frac{3n_3 + 2n_2 + n_1 + n_0}{3N} \times 100$$

wherein

N represents the total number of the plant stems observed, $n_0$ represents the number of stems which were not infested, $n_1$ represents the number of stems which were infested only over the area extending from the lower portion of the first leaf sheath portion, $n_2$ represents the number of stems which were infested only over the area extending from the lower portion to the second leaf sheath portion, and $n_3$ represents the number of stems which were infested over the area extending from the lower portion to at least the third leaf sheath portion.

The test results are shown in Table 2.

Table 2

| Compound No. | Test result against *Pellicularia sasakii* | | |
|---|---|---|---|
| | Concentration of active ingredient (%) | Degree of infection (%) | Phytotoxicity |
| 1 | 0.0125 | 0 | — |
| | 0.025 | 0 | — |
| | 0.05 | 0 | — |
| 2 | 0.0125 | 0 | — |
| | 0.025 | 0 | — |
| | 0.05 | 0 | — |
| 3 | 0.025 | 1.0 | — |
| | 0.05 | 0 | — |
| 4 | 0.05 | 17.3 | — |
| | 0.1 | 9.5 | — |
| 5 | 0.05 | 20.6 | — |
| | 0.1 | 11.0 | — |
| 6 | 0.1 | 18.7 | — |
| 7 | 0.05 | 25.3 | — |
| | 0.1 | 8.5 | — |
| 8 | 0.1 | 20.0 | — |
| 9 | 0.1 | 17.0 | — |
| 10 | 0.1 | 20.3 | — |
| 11 | 0.1 | 12.7 | — |
| 12 | 0.025 | 3.5 | — |
| | 0.5 | 0 | — |
| "V-1" (Comparison Compound) | 0.05 | 73.6 | — |
| | 0.1 | 54.8 | — |
| "Polyoxine" (Commercial Product; comparison) | 0.0045 | 21.5 | — |
| "Monzent" (Commercial product; comparison) | 0.008 (as Urbazid) | 2.0 | + |
| No treatment | | 78.3 | |

Notes:

1) "V-1":

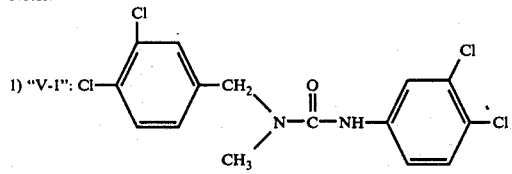

The compound is disclosed in Japanese Patent Publication No. 29252/1969.
2) "Polyoxine": As polyoxine complex
3) "Monzet": As Monzet 80 wp.
4) "—" means none, "+" means some

EXAMPLE 13

Test against *Rhizoctonia solani* (Damping-off)

This test example refers to the treatment of soil with the active compounds to control the soil-borne ineffective fungus, *Rhizoctonia solani*, which causes the damping-off of young seedlings of various crop plants.

Preparation of active compound

To produce a suitable preparation of active compound 3 parts by weight of active compound were mixed with 97 parts of talc to form a powdery mixture.

Test procedures

*Rhizoctonia solani*, which had been grown in a bran medium for 10 days, was inoculated into an upland field soil (clay loam) to form "an inoculated soil". Then the preparation of active compound mentioned above was introduced into the soil so that it contained the compound at the desired concentration. In this treatment, a thorough mixing was carried out. The treated soil and the untreated soil (control sample) each were placed in plastic boxes having an area of 27×18 (cm) and a depth of 9 (cm). Into these boxes, seeds of cucumber and egg plant were sowed in an amount of 50 grains per box. The boxes were placed in a greenhouse and maintained under ordinary plant growth conditions. At regular time intervals, the plants were observed to record the number of the seedlings which had been infested, and also to check the phytotoxicity of the active compound. Twenty-five days after the sowing the total number of infested seedlings was recorded.

The test results are shown in Table 2.

Table 3

| | Test result against *Rhizoctonia solani* | | | | |
|---|---|---|---|---|---|
| | concentration of active ingredient (ppm) | Cucumber | | Egg Plant | |
| Compound No. | | Degree of Infection (%) | Phytotoxicity | Degree of Infection (%) | Phytotoxicity. |
| 1 | 12.5 | 0 | — | 0 | — |
| | 25 | 0 | — | 0 | — |
| | 50 | 0 | — | 0 | — |
| 2 | 50 | 6.5 | — | 3.8 | — |
| 4 | 25 | 8.5 | — | 5.0 | — |
| | 50 | 0 | — | 0 | — |
| "V-1" (Comparison compound | | | | | |
| "PCNB" (Commercial product; comparison | 50 | 100 | — | 100 | — |
| | 50 | 10.0 | — | 5.0 | — |
| No treatment | | 100 | | 100 | |

1) Concentration of active ingredient means the weight ppm of active compound based on the volume of soil
2) "V-1" in this table has the same meaning as in Table 2.
3) "PCNB": Pentachloronitrobenzene It will be appreciated that the instant specification and examples are set forth by way of illustration and not limitation, and that various modifications and changes may be made without departing from the spirit and scope of the present invention.

What is claimed is:

1. An N-4-halobenzyl-N-cycloalkyl-N'-phenyl urea or thiourea of the formula

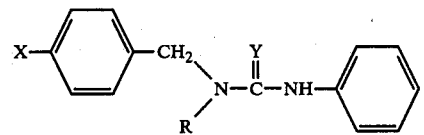

in which
R is cycloalkyl or methyl-cycloalkyl,
X is halogen, and
Y is oxygen or sulfur.

2. A urea or thiourea according to claim 1, in which R is cycloalkyl of 3 to 7 carbon atoms or a methyl-substitution product thereof, and X is chlorine or bromine.

3. A urea or thiourea according to claim 1, wherein such compound is N-4-chlorobenzyl-N-cyclopentyl-N'-phenylurea of the formula

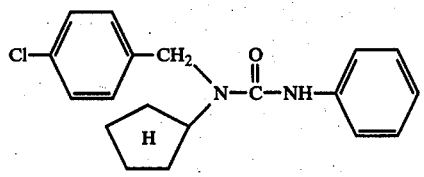

4. A urea or thiourea according to claim 1, wherein such compound is N-4-chlorobenzyl-N-cyclopentyl-N'-phenylthiourea of the formula

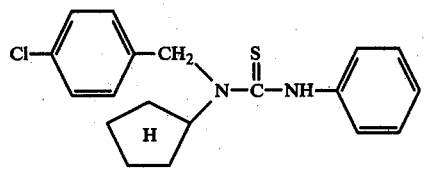

5. A urea or thiourea according to claim 1, wherein such compound is N-4-bromobenzyl-N-cylcopentyl-N'-phenylthiourea of the formula

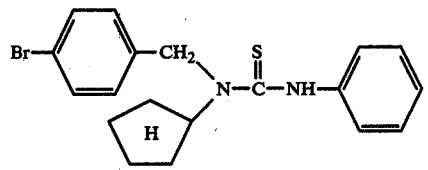

6. A urea or thiourea according to claim 1, wherein such compound is N-4-chlorobenzyl-N-cyclohexyl-N'-phenylthiourea of the formula

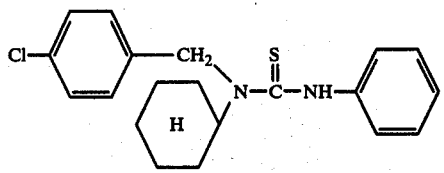

7. A urea or thiourea according to claim 1, wherein such compound is N-4-bromobenzyl-N-cyclopentyl-N'-phenylurea

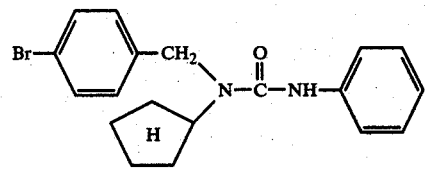

8. A fungicidal composition comprising as active ingredient a fungicidally effective amount of a compound according to claim 1 and a diluent.

9. A method of combating fungi which comprises applying to the fungi or a fungus habitat a fungicidally effective amount of a compound according to claim 1.

10. The method according to claim 9, wherein, such compound is
N-4-chlorobenzyl-N-cyclopentyl-N'-phenylurea,
N-4-chlorobenzyl-N-cyclopentyl-N'-phenylthiourea,
N-4-bromobenzyl-N-cyclopentyl-N'-phenylthiourea,
N-4-chlorobenzyl-N-cyclohexyl-N'-phenylurea, or
N-4-bromobenzyl-N-cyclopentyl-N'-phenylurea.

* * * * *